United States Patent [19]

Babine et al.

[11] Patent Number: 4,760,140

[45] Date of Patent: Jul. 26, 1988

[54] 3-SUBSTITUTED-7-[5-SUBSTITUTED-2-THIAZOLYL)AMINO]-8-OXO-5-THIA-1-AZABICYCLO[4.2.0]OCT-3-ENE-2-CARBOXYLIC ACID, DIPHENYLMETHYL ESTERS

[75] Inventors: Robert Babine, Pomona; Ving J. Lee, Monsey, both of N.Y.

[73] Assignee: American Cyanamid Company, Stamford, Conn.

[21] Appl. No.: 920,399

[22] Filed: Oct. 20, 1986

[51] Int. Cl.$^4$ .................. C07D 501/18; A61K 31/545
[52] U.S. Cl. .................................... 540/228; 540/227; 540/229
[58] Field of Search ....................... 540/227, 228, 229

[56] References Cited

U.S. PATENT DOCUMENTS 4,463,173  7/1984  Jung .................. 540/228 X
4,665,065  5/1987  Miyake et al. .......... 540/222 X

*Primary Examiner*—Donald G. Daus
*Assistant Examiner*—William A. Teoli, Jr.
*Attorney, Agent, or Firm*—Alan M. Gordon

[57] ABSTRACT

Compounds of the formula:

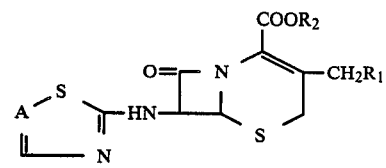

wherein $R_1$ is hydrogen, alkyl($C_1$–$C_3$), vinyl, acetyloxy or

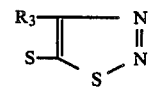

wherein $R_3$ is hydrogen or alkyl($C_1$–$C_6$); $R_2$ is hydrogen or diphenylmethyl and A is $R_4$—C, where $R_4$ is acetyl or benzoyl, are useful as intermediates in the preparation of biologically active cephalosporin derivatives.

7 Claims, No Drawings

3-SUBSTITUTED-7-[5-SUBSTITUTED-2-THIAZOLYL)AMINO]-8-OXO-5-THIA-1-AZABICYCLO[4.2.0]OCT-3-ENE-2-CARBOXYLIC ACID, DIPHENYLMETHYL ESTERS

SUMMARY OF THE INVENTION

This invention is concerned with compounds of the formula:

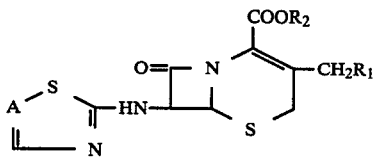

wherein $R_1$ is hydrogen, alkyl($C_1$–$C_3$), vinyl, acetyloxy or

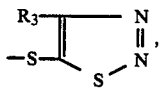

where $R_3$ is hydrogen or alkyl($C_1$–$C_6$); $R_2$ is hydrogen or diphenylmethyl and A is $R_4$—C, where $R_4$ is acetyl or benzoyl.

This invention is further concerned with processes for the production of these compounds as well as their use as intermediates in the preparation of biologically active cephalosporin derivatives.

DESCRIPTION OF THE INVENTION

The compounds of this invention may be prepared according to the following reacting scheme:

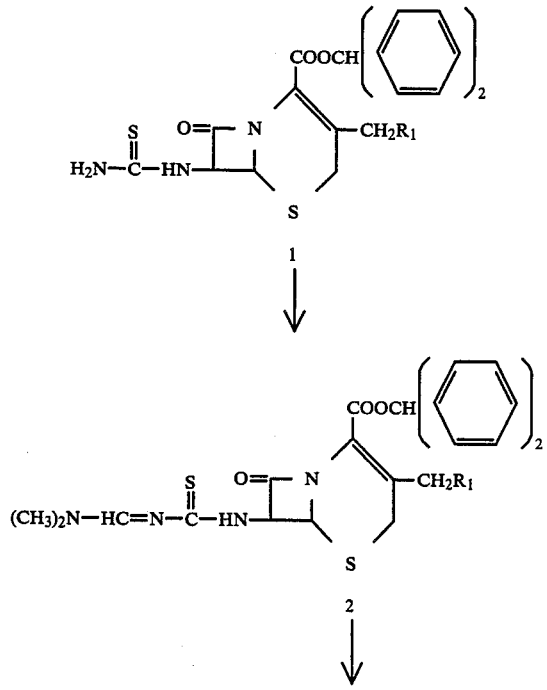

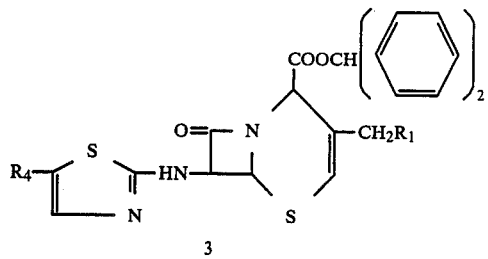

According to the above reaction scheme a 3-substituted-7-[(amionthioxomethyl)amino]-8-oxo-5-thia-1-azabicyclo[4.2.0]oct-2-ene-2-carboxylic acid, diphenylmethyl ester 1, where $R_1$ is as described above, is reacted with N,N-dimethylformamide diethylacetal in dichloromethane, giving the 3-substituted-7-[[[[(dimethylamino)methylene]amino]thioxomethyl]amino]-8-oxo-5-thia-1-azabicyclo[4.2.0]oct-2-ene-2-carboxylic acid, diphenylmethyl ester 2, which is reacted with a 2-bromo-substituted ethanone of the formula $R_4COCH_2Br$, where $R_4$ is as described above, and potassium carbonate in acetonitrile, giving the product 3.

The diphenylmethyl ester 3 may be converted to the free carboxylic acid where $R_2$ is hydrogen, by treatment with anisole and trifluoroacetic acid in dichloromethane.

The compounds of this invention where $R_2$ is hydrogen are biologically active and possess antibacterial activity when tested by the Mueller-Hinton agar dilution method against a variety of organisms. The results of this test with representative compounds of this invention appear in Table I.

TABLE I

In vitro Antibacterial Activity

| | Minimal Inhibitory Concentration (mcg/ml) Compound of Example No. | |
|---|---|---|
| Organism | 5 | 6 |
| *Escherichia coli* CMC 84-11 | >128 | >128 |
| *Escherichia coli* 311 | >128 | >128 |
| *Escherichia coli* ATCC 25922 | >128 | >128 |
| *Klebsiella pneumoniae* CMC 84-5 | 128 | >128 |
| *Klebsiella pneumoniae* AD | 32 | 128 |
| *Klebsiella oxytoca* IO 83-1 | >128 | >128 |
| *Enterobacter cloacae* CMC 84-4 | >128 | >128 |
| *Enterobacter aeruginosa* IO 83-44 | >128 | >128 |
| *Serratia marcescens* CMC 83-27 | >128 | >128 |
| *Serratia marcescens* F-35 | >128 | >128 |
| *Proteus rettgherii* IO 83-21 | >128 | >128 |
| *Morganella morganii* IO 83-18 | >128 | >128 |
| *Providencia stuartii* CMC 83-82 | >128 | >128 |
| *Citrobacter diversis* K 82-24 | 128 | >128 |
| *Citrobacter freundii* IO 83-13 | >128 | >128 |
| Acinetobacter CMC 83-89 | >128 | >128 |
| Acinetobacter IO 83-49 | >128 | >128 |
| *Pseudomonas aeruginsa* CMC 83-19 | >128 | >128 |
| *Pseudomonas aeruginsa* 12-4-4 | >128 | >128 |
| *Pseudomonas aeruginosa* ATCC 27853 | >128 | >128 |
| *Staphylococcus aureus* SSC 82-31 | 1 | 0.12 |
| *Staphylococcus aureus* ATCC 25923 | 1 | 0.12 |
| *Staphylococcus aureus* SSC 82-20 | 4 | 1 |
| *Staphylococcus aureus* SSC 82-26 | 2 | 1 |
| *Staphylococcus aureus* SSC 82-24 | 128 | 64 |
| *Staphylococcus aureus* SSC 82-57 | 128 | 128 |
| *Staphylococcus epidermidis* CMC 83-133 | 1 | 0.12 |
| *Staphylococcus epidermidis* ATCC 12228 | 2 | 1 |
| Enterococcus CMC 83-53 | 128 | 32 |
| *Streptococcus faecalis* ATCC 29212 | 64 | 16 |
| *Micrococcus lutea* PCI 1001 | 2 | 1 |

TABLE I-continued

In vitro Antibacterial Activity

| | Minimal Inhibitory Concentration (mcg/ml) Compound of Example No. | |
|---|---|---|
| Organism | 5 | 6 |
| *Bacillus subtilis* ATCC 6633 | 0.25 | 0.5 |

EXAMPLE 1

(6R-trans)-3-[(Acetyloxy)methyl]-7-[[[[(dimethylamino)methylene]amino]thioxomethyl]amino]-8-oxo-5-thia-1-azabicyclo[4.2.0]oct-2-ene-2-carboxylic acid, diphenylmethyl ester A 650 mg portion of N,N-dimethylformamide diethylacetal in 10 ml of dichloromethane was added dropwise to a solution of 2 g of (6R-trans)-3-[(acetyloxy)-methyl-7-[(aminothioxomethyl)amino]-8-oxo-5-thia-1-azabicyclo[4.2.0]oct-2-ene-2-carboxylic acid, diphenylmethyl ester in 35 ml of dichloromethane. The mixture was stirred for 20 minutes, then filtered, evaporated and the residue purified by flash chromatography using the system ethyl acetate:petroleum ether (1:1) and giving 1.08 g of the desired product.

EXAMPLE 2

[2R-(2α,6α,7β)]-3-[(Acetyloxy)methyl]-7-[(5-benzoyl-2-thiazolyl)amino]-8-oxo-5-thia-1-azabicyclo[4.2.0]oct-3-ene-2-carboxylic acid, diphenylmethyl ester A mixture of 940 mg of (6R-trans)-3-[(acetyloxy)methyl]-7-[[[[(dimethylamino)methylene]amino]thioxomethyl]amino]-8-oxo-5-thia-1-azabicyclo[4.2.0]oct-2-ene-2-carboxylic acid, diphenylmethyl ester, 380 mg of 2-bromo-1-phenylethanone, 235 mg of potassium carbonate and 30 ml of acetonitrile was reacted as described in Example 1, giving 900 mg of the desired compound.

EXAMPLE 3

(6R-trans)-3-[(Acetyloxy)methyl]-7-[(5-benzoyl-2-thiazolyl)amino]-8-oxo-5-thia-1-azabicyclo[4.2.0]oct-2-ene-2-carboxylic acid, diphenylmethyl ester A mixture of 720 mg of (6R-trans)-3-[(acetyloxy)methyl]-7-[[[[(dimethylamino)methylene]amino]thioxomethyl]amino]-8-oxo-5-thia-1-azabicyclo[4.2.0]oct-2-ene-2-carboxylic acid, diphenylmethyl ester, 260 mg of 2-bromo-1-phenylethanone and 90 mg of potassium carbonate in 15 ml of dry acetonitrile was stirred for about 1 hour, then filtered and the filtrate evaporated, giving 526 mg of the desired product.

EXAMPLE 4

(6-R-trans)-3-[(Acetyloxy)methyl]-7-[(5-acetyl-2-thiazolyl)amino]-8-oxo-5-thia-1-azabicyclo[4.2.0]oct-2-ene-2-carboxylic acid, diphenylmethyl ester A mixture of 585 mg of (6R-trans)-3-[(acetyloxy)methyl]-7-[[[[(dimethylamino)methylene]amino]thioxomethyl]amino]-8-oxo-5-thia-1-azabicyclo[4.2.0]oct-2-ene-2-carboxylic acid, diphenylmethyl ester, 127 mg of propionyl chloride, 188 mg of sodium iodide and 15 ml of acetontrile was stirred for 90 minutes, then 99 mg of pyridine was added. This mixture was stirred for 90 minutes, then dichloromethane was added and the mixture was refluxed for 20 minutes. The solution was washed with 10% hydrochloric acid, brine and aqueous sodium bicarbonate, dried and evaporated, giving 418 mg of the desired product.

EXAMPLE 5

(6R-trans)-3-[(Acetyloxy)methyl]-7-[(5-acetyl-2-thiazolyl)amino]-8-oxo-5-thia-1-azabicyclo[4.2.0]oct-2-ene-2-carboxylic acid A mixture of 255 mg of (6R-trans)-3-[(acetyloxy)methyl]-7-[(5-acetyl-2-thiazolyl)amino]-8-oxo-5-thia-1-azabicyclo[4.2.0]oct-2-ene-2-carboxylic acid, diphenylmethyl ester was reacted with anisole and trifluoroacetic acid in dichloromethane with stirring at 0° C. for 30 minutes, then at room temperature for 30 minutes. The addition of ether and petroleum ether gave a precipitate which was washed with ether, giving 135 mg of the desired product as a pale yellow powder.

EXAMPLE 6

(6R-trans)-3-[(Acetyloxy)methyl]-7-[(5-benzoyl-2-thiazolyl)amino]-8-oxo-5-thia-1-azabicyclo[4.2.0]oct-2-ene-2-carboxylic acid A 235 mg portion of (6R-trans)-3-[(Acetyloxy)methyl]7-[(5-benzoyl-2-thiazolyl)amino]-8-oxo-5-thia-1-azabicyclo[4.2.0]oct-2-ene-2-carboxylic acid, diphenylmethyl ester was reacted with anisole and trifluoroacetic acid in dichloromethane as described in Example 5, giving 143 mg of the desired product as a pale yellow powder.

EXAMPLE 7

(6R-trans)-3-[(Acetyloxy)methyl]-8-oxo-7-(1,2,4-thiadiazol-5-ylamino)-5-thia-1-azabicyclo[4.2.0]oct-2-ene-2-carboxylic acid, diphenylmethyl ester A mixture of 60 mg of (6R-trans)-3-[(acetyloxy)methyl]-7-[[[[(dimethylamino)methylene]amino]thioxomethyl]amino]-8-oxo-5-thia-1-azabicyclo[4.2.0]oct-2-ene-2-carboxylic acid, diphenylmethyl ester, 14 mg of hydroxylamine-O-sulfonic acid and 17.14 mg of pyridine in a mixture of 3 ml of ethanol and 1 ml of methanol was stirred at room temperature. A 0.5 ml portion dioxane was added to enhance solubility. After 1 hour the mixture was concentrated, dichloromethane added to the residue, the solution washed with 10% hydrochloric acid and brine, then decolorized, filtered and evaporated, giving the desired product.

What is claimed is:

1. A compound selected from those of the formula:

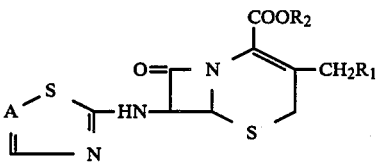

wherein $R_1$ is hydrogen, alkyl($C_1$-$C_3$), vinyl, acetyloxy or

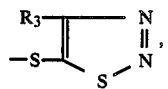

where $R_3$ is hydrogen or alkyl($C_1$-$C_6$); $R_2$ is hydrogen or diphenylmethyl; and A is $R_4$—C, where $R_4$ is acetyl or benzoyl.

2. The compound according to claim 1, [2R-(2α,-6α,7β,)]-3-[(acetyloxy)methyl]-7-[(5-benzoyl-2-thiazolyl)amino]-8-oxo-5-thia-1-azabicyclo[4.2.0]oct-3-ene-2-carboxylic acid, diphenylmethyl ester.

3. The compound according to claim 1, (6R,-trans)-3-[(acetyloxy)methyl]-7-[(5-benzoyl-2-thiazolyl)amino]-8-oxo-5-thia-1-azabicyclo[4.2.0]oct-2-ene-2-carboxylic acid, diphenylmethyl ester.

4. The compound according to claim 1, (6R-trans)-3-[(acetyloxy)methyl]-7-[(5-acetyl-2-thiazolyl)amino]-8-oxo-5-thia-1-azabicyclo[4.2.0]oct-2-ene-2-carboxylic acid, diphenylmethyl ester.

5. The compound according to claim 1, (6R-trans)-3-[(acetyloxy)methyl]-7-[(5-acetyl-2-thiazolyl)amino]-8-oxo-5-thia-1-azabicyclo[4.2.0]oct-2-ene-2-carboxylic acid.

6. The compound according to claim 1, (6R-trans)-3-[(acetyloxy)methyl]-7-[(5-benzoyl-2-thiazolyl)amino]-8-oxo-5-thia-1-azabicyclo[4.2.0]oct-2-ene-2-carboxylic acid.

7. The compound (6R-trans)-3-[(acetyloxy)methyl]-7-[[[[(dimethylamino)methylene]amino]thioxomethyl]amino]-8-oxo-5-thia-1-azabicyclo[4.2.0]oct-2-ene-2-carboxylic acid, diphenylmethyl ester.

* * * * *